United States Patent [19]

Flink

[11] Patent Number: 4,566,849
[45] Date of Patent: Jan. 28, 1986

[54] PRESSURE MEDIUM DRIVEN MACHINE TOOL

[75] Inventor: Claes H. Flink, Åmål, Sweden

[73] Assignee: Aktiebolaget IRO, Ulricehamn, Sweden

[21] Appl. No.: 557,284

[22] PCT Filed: Mar. 8, 1983

[86] PCT No.: PCT/EP83/00067
§ 371 Date: Oct. 21, 1983
§ 102(e) Date: Oct. 21, 1983

[87] PCT Pub. No.: WO83/03119
PCT Pub. Date: Sep. 15, 1983

[30] Foreign Application Priority Data

Mar. 8, 1982 [SE] Sweden ................ 8201404

[51] Int. Cl.$^4$ ............ F01D 15/16; B23Q 5/06; B24B 47/14
[52] U.S. Cl. ............ 415/92; 415/202; 415/503; 433/132
[58] Field of Search ............ 415/53 T, 90, 92, 202, 415/503; 433/132

[56] References Cited

U.S. PATENT DOCUMENTS

| | | | |
|---|---|---|---|
| 2,763,461 | 9/1956 | Hill | 415/503 X |
| 3,147,551 | 9/1964 | Seegers | 415/503 X |
| 3,364,576 | 1/1968 | Kern, Jr. | 433/132 X |
| 4,141,674 | 2/1979 | Schönwald | 415/53 T X |
| 4,347,034 | 8/1982 | Vigh | 415/92 |

FOREIGN PATENT DOCUMENTS

| | | |
|---|---|---|
| 591352 | 7/1925 | France . |
| 1320802 | 2/1963 | France . |
| 547777 | 9/1942 | United Kingdom . |

OTHER PUBLICATIONS

IBM Technical Disclosure Bulletin, vol. 13, No. 7, Dec. 1970, "Air Driven Motor", p. 1982.

Primary Examiner—Robert E. Garrett
Assistant Examiner—Joseph M. Pitko
Attorney, Agent, or Firm—Flynn, Thiel, Boutell & Tanis

[57] ABSTRACT

Machine tool having a jet turbine driving a rotatable spindle with a tool holder, said spindle is comprised in a spindle housing, said jet turbine consisting of a disc-shaped turbine rotor being closely enclosed by a turbine housing, said turbine rotor having peripherally arranged discrete recesses, each recess having a concave front actuation wall for the jet and one sidewardly arranged outlet opening which opens in the axial direction of the rotor, said housing having at least one inlet nozzle for the jet directed into the recesses and having at least one outlet opening for the spent jet medium. Known machine tools suffer under strong speed losses when the load increases or varies. This disadvantage results from a constant interference between spent air within the recesses and the working jet. Thus, the energy of the jet cannot be used with good efficiency. According to the present invention the energy of the jet can be used with better efficiency, since the inlet nozzle is directed towards the deepest section of the front concave actuation wall by impacting on this wall and since there is provided a guiding path and an additional expansion space below the jet which in combination produce a pumping effect for quickly disposing the spent jet medium. The expansion space is provided by the concave rear wall and the flat bottom of the recess. The guiding path is defined by the concave side wall together with the flat bottom and the concave rear wall.

11 Claims, 7 Drawing Figures

PRESSURE MEDIUM DRIVEN MACHINE TOOL

FIELD OF THE INVENTION

The invention relates to a jet turbine driven machine tool having a jet turbine driving a rotatable spindle with a tool holder, said spindle is comprised in a spindle housing, said jet turbine consisting of a disc-shaped turbine rotor closely enclosed by a turbine housing, said turbine rotor having peripherally arranged discrete recesses, each recess having a concave front actuation wall for the jet and one sidewardly arranged outlet opening which opens in the axial direction of the rotor, said housing having at least one inlet nozzle for the jet directed into the recesses and having at least one outlet opening for the spent jet medium.

BACKGROUND OF THE INVENTION

A known machine tool (SE 418 259) has a turbine rotor with turbine blades provided at the periphery. Each pair of blades forms together with the adjacent inner wall of the turbine housing a chamber which is open at two axially opposed sides of the rotor. Especially the spent and expanded medium which leaves the chamber at the side opposite to the outlet opening of the housing contacts the stationary part of the housing and interferes with the fresh medium entering the chamber during the next revolution of the turbine rotor. A disadvantage resulting from the constant interference between spent and fresh medium is the weak "braked power" ability of the machine tool when working in various sorts of material and under increasing or varying load conditions. With this ability is meant that the machine tool should keep a constant speed despite any variations in load.

Another known machine tool (GB No. 547 777) has a disc-shaped turbine rotor with discrete recesses in the periphery which are spaced apart in circumferential direction. From the bottom of each recess a radial bore leads to radial inwardly provided axial outlet channels. Additionally an inclined bore begins in the front or actuation wall of each recess and leads into the radial bore of the next following recess. Interferences between fresh supplied medium and the spent and expanded medium cannot be avoided and a certain part of the jet energy is wasted for the disposal of the medium through the long channels. Furthermore, the manufacture of the rotor is unduly expensive.

U.S. Pat. No. 845,059 describes a jet turbine with a disc-shaped turbine rotor having approximately semi-circular pockets in one side surface separated by partition walls. The pockets and the partition walls are inclined in the jet flow direction. Each pocket consists of three staggered steps of equal length. Each step has one curved front actuation surface. The jet enters the pocket on one side, is deviated along the actuation surface and leaves the pocket at the opposite side where an outlet opening is provided. During its way along the surface the jet produces a reaction force which drives the rotor. The jet only works in one pocket for a very short time period. For the longer time, it is split up and has to actuate two pockets simultaneously. A significant part of the jet energy is necessary to clear the pockets of expanded medium. Nevertheless, a certain amount of expanded medium rests within each pocket and interferes with the next jet dose entering during the next revolution.

Finally, U.S. Pat. No. 848,587 describes a jet turbine having a disc-like rotor with approximately semi-circular pocket shaped recesses in one side of the disc or in the periphery respectively. The pockets are inclined in the jet direction. Each pocket is separated from the adjacent ones by partition walls and consists of one main pocket part and one staggered supplemental pocket part within the main pocket part. Between the parts of the pocket a partition wall is provided which is cut out at the inlet side of the pocket to define a narrow inlet opening to the main pocket part. The jet enters each pocket or pocket part at one side, is then deviated along the semi-circular surfaces and leaves the pocket at the opposite side where outlet openings are provided. The pockets are difficult to manufacture and there cannot be avoided interferences between the jet and the expanded medium as well as between the jet and the partition walls. This known turbine also is a reaction turbine which is driven by deviating the jet.

It is one task of the invention to improve the jet turbine in a machine tool as explained above. Said jet turbine ought to be simple in manufacture and less expensive than the known devices and has an improved efficiency by avoiding significant interferences between the jet and the spent or expanded medium in each recess.

It is furthermore an object of the invention to improve the ability of such a machine tool to keep an essentially constant and high working speed despite variations in load, that means to increase the so-called "braked power" ability of the machine tool.

These objects are achieved with a jet turbine, wherein the inlet nozzle is directed towards the deepest section of the front and concave actuation wall, that each recess is provided with a concave side wall opposite to the outlet opening and also is provided with a concave rear wall opposite to the front actuation wall, that there is provided a flat bottom surrounded by the front actuation wall, the side wall and the rear wall which are interconnected with each other, and that the bottom is inclined downwardly opposite to the flow direction of the jet when the jet initially impacts against the front wall so that said rear, side and bottom walls define an expansion space below the jet with increasing depth towards the rear wall, and also defining a guiding path towards the outlet opening for the expanding jet medium.

Since the jet is directed to the deepest section of the front surface and since additionally the form of the rear wall leads to greater peripheral length of the recess, this allows the jet to actuate the front surface for a long time period and with its direct impact force, each recess works very efficiently. The turbine does work as an action turbine with the impact forces of the jet and not, as it is known from the prior art, as a reaction turbine with jet deviation (i.e. bending). The turbine rotor is simple to manufacture since the configuration of each recess is very simple. The most important advantage of this construction lies in the fact that the jet is not interfered with by the expanding medium since there occurs a pumping effect from the expansion space along the guiding path for the expanding medium. Due to the rotational movement of the recess (in the jet working direction) the medium rebounding from the front wall is forced along the side wall and the rear wall towards the outlet opening, which movement is assisted by a pumping effect which takes place below the jet. In the expansion space near the rear wall, said expansion space having a triangular cross section as seen in the axial direction of the rotor there exists lower pressure than near the front wall, due to the fact that in and near the boundary layer of a medium jet low pressure is produced which in that case helps to suck the expanding medium away from the area of the front wall where the jet impacts. Under the continuous acceleration of the rotor and during and after the working period of the jet in each recess, the mass of caught medium is forced along the guiding path and through the outlet opening. When each recess again passes the inlet nozzle, it is completely emptied and ready for a new working period under the same positive working conditions as before. Since each recess only is open towards the exhaust outlet opening of the housing and the spent medium is disposed very quickly, considerably improved flow conditions have been achieved as compared with the prior art turbines, which directly improves the braked power ability of the machine tool driven by the jet turbine. This is the main reason why the tool machine driven by the jet turbine is so strong that it can keep a high, essentially constant working speed despite increasing or varying load conditions. The efficiency of the medium jet is considerably raised. A machine tool with a jet turbine according to the invention has a run away speed of approximately 80,000 r.p.m. at a medium pressure of 6 bars, whereas the working speed at normal load conditions is kept at approximately 74,000 r.p.m.

Due to the advantageous pressure medium flow conditions, the noise level of the machine tool is extremely low, which of course is important from the working environment point of view.

Advantageous embodiments of the invention are contained in the depending claims.

BRIEF DESCRIPTION OF THE DRAWINGS

Further features and advantages of the invention will be apparent from the following description of embodiments, wherein.

DETAILED DESCRIPTION

Figure 1:
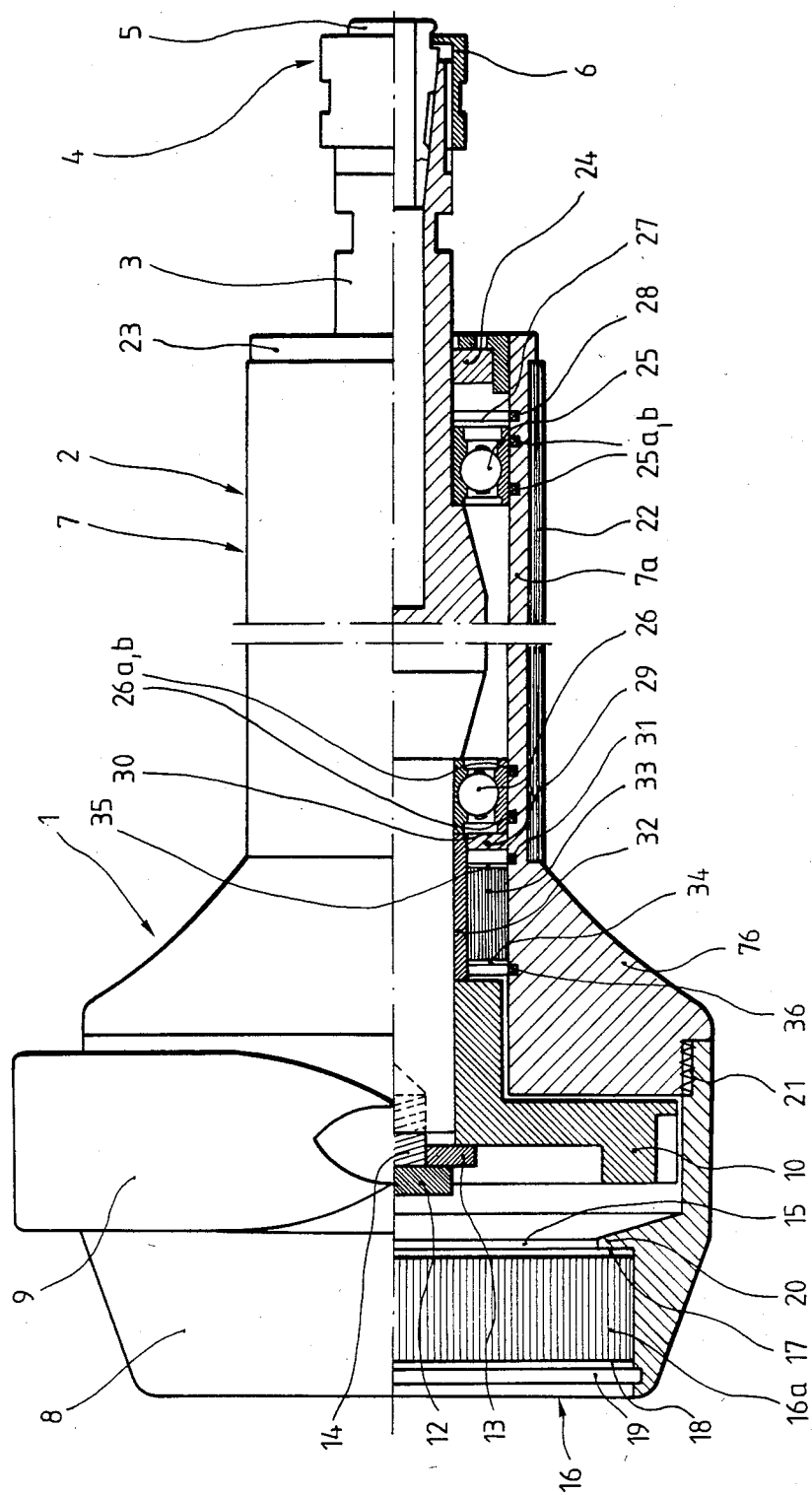
FIG. 1 is a partially cut away sectional view of a machine tool with a jet turbine according to the invention.
Figure 2:
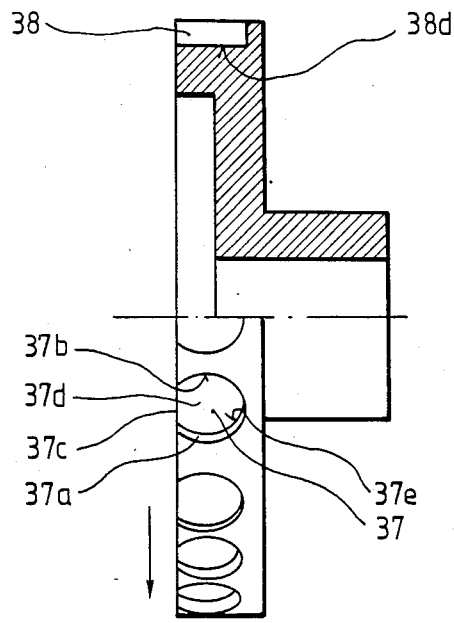
FIG. 2 is a partially sectional view of a first embodiment of a turbine rotor according to the invention.
Figure 3:
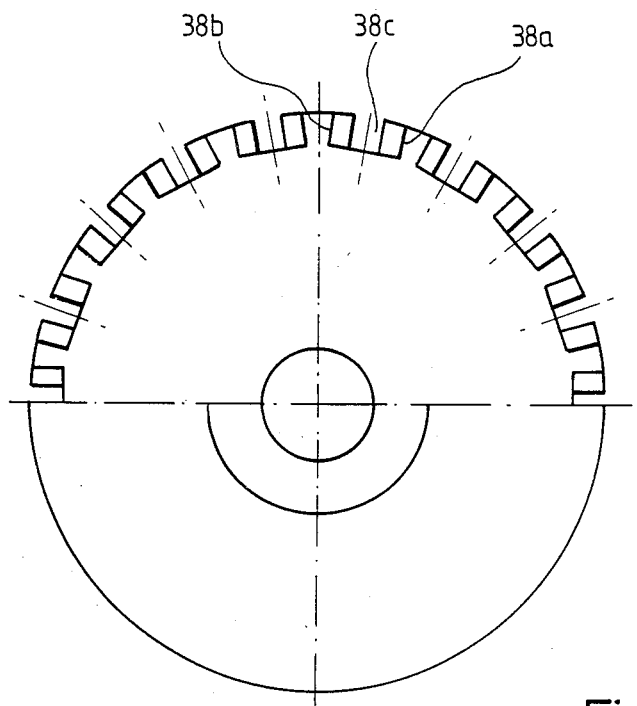
FIG. 3 is a rear view of the turbine rotor of FIG. 2.

A tool machine (FIG. 1) has a turbine housing 1 and a spindle housing 2. A spindle 3 extends from the interior of the turbine housing 1, through the spindle housing 2 and ends up with a chuck 4, comprised by a collet 5 and a clamp nut 6, for clamping a tool, e.g. a grinding pin, a milling tool, a hard metal file, an engraving pin or a drill. The machine tool body consists of two parts, namely a handle 7 and a cap-housing 8. The handle 7 extends with a sleeve 7a and a collar 7b into the spindle housing 2. The cap-housing 8 is provided with a tangential pressure medium inlet nozzle 9, which e.g., at its orifice has a diameter of 1.6 mm. The collar 7b and the cap-housing 8 are attached together by threads 21.

In the turbine housing, a turbine rotor 10 in accordance with the invention is arranged, the design of which can be seen from FIGS. 2-7. The rotor 10 is preferably made of aluminium, and is fixed to the rear end of the spindle 3 by means of threads 14, a nut 12 and a washer 13. In the cap-housing 8, a hole 15 is provided which is the exhaust opening for the consumed or spent pressure medium. The hole 15 contains a noise damper body 16, 16a, covered by perforated plates 17 and 18. The damper 16, 16a is fixed by means of a locking wire 19 against a shoulder 20 in the hole 15. The damper body 16, 16a consists of an air pervious, air absorbing material, preferably POROLON, which is the trade name for a certain kind of compressed foam rubber. The damper body 16, 16a also distributes the exhaust medium so that it does not trouble the operator. The exhaust opening 15 occupies an area which essentially corresponds to the cross sectional area of the turbine rotor 10.

The sleeve 7a is covered by a shrunk-on plastic tube 22. The spindle housing 2 ends near the chuck 4 with an end plate 23 which is pressed into the sleeve 7a and has an opening for the spindle 3. In the end plate 23 a dust collector 24 of felt is arranged to prevent particles from entering the spindle housing 2. The spindle 3 is journalled in the spindle housing 2 with ball bearings 25, 26 and is sealed by rubber O-rings 25a, b and 26a, b. The ball bearing 25 is secured by a washer 27 and a locking wire 28. The ball bearing 26 is secured with a spring washer 29, a plane plate 30 and a locking wire 31. The ball bearings 25, 26 are permanently lubricated. This means that the bearings are lubricated only in connection with maintenance of the machine tool, in contrary to lubrication methods that are based on a constant or intermittent supply of lubricants to the bearings.

A spacing sleeve 32 is placed between the turbine rotor 10 and the inner race of the ball bearing 26 and is pressed onto the spindle 3. Its outer surface is machined with very small tolerances and is very smooth. A seal 33 in the form of a sleeve of graphite is pressed between the spacing sleeve 32 and the collar 7b. Cover washers 34, 35 are positioned on opposite sides of the seal 33. The seal 33 with the cover washers 34, 35 is kept in place on one side by a locking wire 31 and on the other side by locking means 36. It has proved to be a very good seal against air leakage between the turbine housing 1 and the spindle housing 2, provided of course that it under a certain force is in contact with the spacing sleeve 32, being pressed onto the spindle 3, as well as with the inner surface of the collar 7b. Despite this certain force, which is thus necessary for the sealing function, a high sliding speed such as 40 m/s can be achieved between the spacing sleeve 32 and the graphite seal 33. In this embodiment of the machine tool, the sliding speed amounts to 25-30 m/s, which thus can easily be tolerated by the graphite seal 33.

The turbine rotor (FIG. 2) has along its periphery a series of identical recesses 37 and 38. The recess 37 is now explained in more detail. It has a front concave actuation wall 37a, which is hit by a dose of the compressed air jet generated in the inlet nozzle 9. It furthermore has a rear, in the opposite direction, concave wall 37b, and has a axial outlet opening 37c towards the exhaust outlet opening 15. Said front and rear walls 37a, 37b form together with a flat bottom surface 37d and a concave side wall 37e together with a closely surrounding inner wall of the cap-housing 8 an appropriate optimal working and expansion space for the compressed air jet dose coming from the inlet nozzle 9.

In this embodiment, the recesses 37 have a circular configuration, e.g., with a diameter of 7.5 mm. This is very advantageous from a manufacturing point of view, since each recess can be made by an easy drilling or milling operation. Each recess has a depth of 2.5 mm. In circumferential direction, equal distances of 0.8775 mm exist between the recesses 37. The center of each circular recess 37 has an axial distance of 2.7 mm to the outlet opening 37c.

Figure 4:
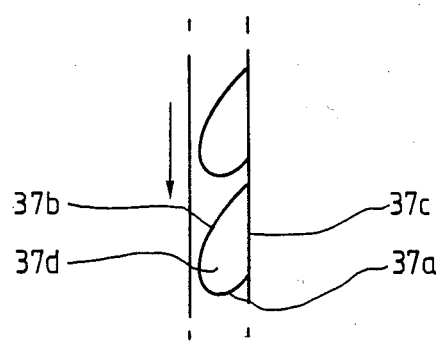
FIG. 4 is a part of a second embodiment of a turbine rotor with modified recesses.

Although the bottom surface 37d is shown in parallel to the axis of the turbine rotor 10, it also can be slightly inclined inwards towards the exhaust outlet opening 37c for further improving the disposal of expanded air. The rear wall 37b can have the concave configuration as shown in FIG. 4 wherein the concave bending decreases towards the outlet opening 37c, for further improving its ability to efficiently dispose of the expanded air from the recess. This form of the recess can be difficult to achieve by machining, but can easily be made by die-casting, when the rotor is made of aluminium or by injection-molding, when it is made of plastic material.

Figure 5:
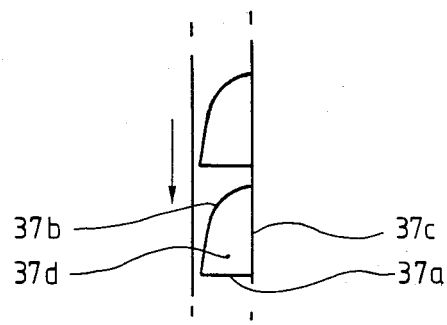
FIG. 5 is a part of a further embodiment of the turbine rotor.

The front actuation wall of the recess could also have a non-circular form. In FIG. 4, it is more concave than in FIG. 2. It could also be straight as shown in FIG. 5. A straight actuation wall has, however, proved to give a lower turbine power.

Figure 6:
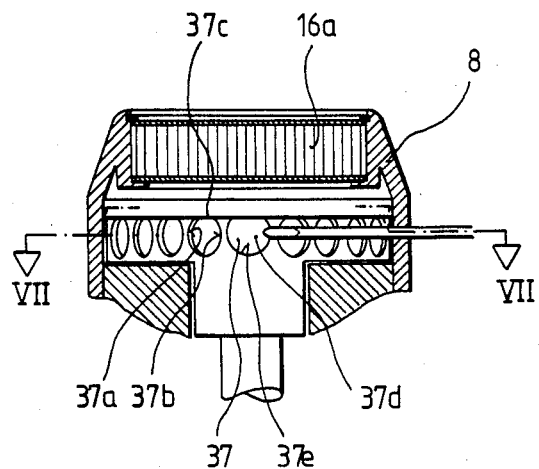
FIG. 6 is a view into the housing of the machine tool of FIG. 1 with several parts cut away.
Figure 7:
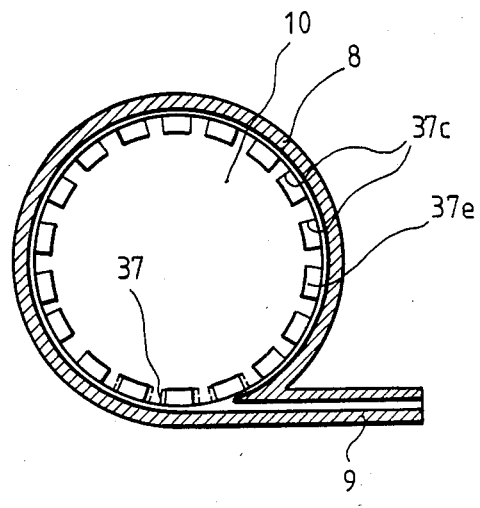
FIG. 7 is a sectional view on the rotor of FIG. 6 along the line VII—VII.

The inlet nozzle 9 is arranged to aim the medium jet into the deepest section of the concave front wall 37a (FIG. 6). That means that the nozzle 9 preferably is arranged in a plane standing perpendicular to the axis of the rotor 10, said plane also contains the centers of all recesses in FIGS. 2 or 6. FIG. 7 shows that the inlet nozzle 9 guides the jet tangentially with respect to the periphery of the turbine rotor 10. As a result, from this arrangement the jet first hits the upper edge of the concave front wall 37a and then furthermore impacts on the whole height of the wall 37a as the rotor moves. Since the recesses 37 have a remarkable extension in the peripheral direction and since the rear wall 37b is concave to the opposite side, the jet will not be interfered with by the upper edge of the rear wall 37b unless a certain and great dose of the jet has hit the front wall. Due to the height of the rear wall 37b and the flat bottom 37d which is inclined backwardly with respect to the jet direction, when the jet hits the front wall 37a an expansion space is produced below the jet. This expansion space has—seen in the axial direction of the rotor—a triangular cross section. Furthermore, the side wall 37e together with the rear wall 37b, the bottom surface 37d and the inner wall of the cap-housing 8 together form an assymetric and curved guiding path towards the outlet opening 37c. Under the acceleration of the turbine rotor 10, the mass of expanding medium is guided along this guiding path, which movement is assisted by the pumping effect of the expansion space below the jet in which space low pressure dominates. The low pressure in this area of the recess results from the physical phenomena that always in the neighbourhood of the boundary layer of a jet, a significant low pressure occurs. The guiding path and the expansion space with low pressure both force the medium rebounding from the front wall 37a towards the outlet opening 37c and are responsible for quickly exhausting the expanded medium. Any significant interference between expanding or expanded medium and the jet is avoided. The turbine can work as in action turbine and is rotated mainly by the impact force of the jet. Since the rebounding medium is exhausted quickly, the jet can work until the partition wall to the next following recess cuts off the jet. The clearing operation in the recess thereafter is continued so that it is ensured that the recess will be empty for the next jet after the completed revolution of the turbine rotor.

In FIG. 7, cap-housing 8 is cut in plane VII—VII of FIG. 6 and the turbine rotor 10 is shown with its backside adjacent the damper body 16a. Only the outlet openings 37c of the recesses 37 are shown, except three of the recesses which are shown in dotted lines.

I claim:

1. In a machine tool having a jet turbine driving a rotatable spindle with a tool holder, said spindle being rotatably supported in a spindle housing, said jet turbine having a disc-shaped turbine rotor closely rotatably enclosed by a turbine housing, said turbine rotor having peripherally arranged discrete recesses, each recess having a concave front actuation wall for the jet and one sidewardly arranged outlet opening which opens in the axial direction of the rotor, said housing having at least one inlet nozzle for the jet directed into the recesses and having at least one outlet opening for the spent jet medium, comprising the improvement wherein: the inlet nozzle is directed circumferentially of and tangentially to the rotor towards the deepest section of the concave front actuation wall; each recess is provided with a concave side wall opposite to the outlet opening and is also provided with a concave rear wall opposite to the front actuation wall; each recess is provided with a flat bottom wall surrounded by the front acutation wall, the side wall and the rear wall which are interconnected with each other; the turbine housing has an unrestricted exhaust opening disposed axially adjacent one end of the rotor in direct communication with the outlet opening; and the bottom wall is inclined backwardly relative to the flow direction of the jet when the jet initially impacts against the front wall so that said side, rear and bottom walls define an expansion space below the jet which is of increasing depth towards the rear wall and also define a guiding path towards the outlet opening for the expanding jet medium.

2. Machine tool according to claim 1, characterised in that there is provided a circumferential distance between the back wall (37b) of one recess (37) and the front wall (37a) of the next following recess.

3. Machine tool according to claim 1, wherein each recess is of circular configuration—seen in radial direction of the rotor—and intersects one axial side of the rotor twice, the outlet opening being defined between the points of intersection.

4. Machine tool according to claim 1, wherein each recess is a radial blind bore in the cylindrical periphery of the turbine rotor and is made by drilling, milling or die-casting.

5. Machine tool according to claim 1, wherein the bottom wall of each recess is inclined towards the outlet opening, wherein the depth of the recess increases towards the outlet opening.

6. Machine tool according to claim 1, wherein the turbine rotor has an outer diameter D, there is provided a number of 0.375 D recesses around the periphery of the rotor with equal intermediate distances of 0.0183 D and with inner diameters of equal 0.156 D, each recess has a radial depth of 0.052 D and the axial distance between the centre of each recess and its outlet opening is about 0.056 D.

7. Machine tool according to claim 1, wherein the concave bending of the rear wall decreases towards the outlet opening, in order to enlarge the circumferential size of the outlet opening.

8. In a tool assembly having a spindle adapted to support thereon a tool holder and rotatably supported within a spindle housing, and a jet turbine for rotatably driving the spindle, the jet turbine including a rotatable disc-shaped rotor which is drivingly coupled to the spindle and is closely rotatably enclosed within a turbine housing, said turbine rotor having a surrounding peripheral wall provided with a plurality of discreet recesses formed therein in angularly spaced relationship therearound, and the turbine housing having an inlet opening for directing a jet of fluid against the rotor and a discharge opening for removing the fluid from the rotor, comprising the improvement wherein the recess projects substantially radially inwardly of the rotor from the surrounding peripheral wall thereof and is defined by a bottom wall and a peripheral side wall, the recess having a depth which is small relative to the cross-section thereof as defined within said peripheral side wall, said recess opening axially through one axial end surface of the rotor for defining an outlet opening from the recess for the discharge of fluid therefrom, said peripheral side wall extending through less than 360° and terminating at said outlet opening, said peripheral side wall including concave front and rear wall portions which are disposed opposite and substantially face one another, said peripheral side wall including a concave side wall portion which is disposed axially opposite the outlet opening and is connected between the front and rear wall portions, said inlet opening extends circumferentially of and substantially tangentially with respect to the peripheral wall of the rotor and positioned so as to direct the jet toward the deepest section of the concave front wall portion so that the jet impinges against the front wall portion in substantially perpendicular relationship thereto, and said discharge opening comprising an enlarged unrestricted flow passage which extends axially of said turbine housing away from said one axial end surface of said turbine rotor, said passage being disposed in open communication with the outlet openings defined by said recesses.

9. An assembly according to claim 8, wherein each said recess is defined by a substantially blind bore which projects radially inwardly from the peripheral surface of the rotor and is of a cylindrical cross-section having a diameter which substantially exceeds the depth of the bore, said bore being positioned with the center line thereof spaced from said one axial end surface of the rotor by a distance which is less than the radius of the bore so that the bore opens axially outwardly through said one axially end surface for defining said outlet opening.

10. An assembly according to claim 8, wherein the peripheral wall of said rotor is substantially cylindrical, said recesses projecting inwardly of said rotor from said peripheral wall, said turbine housing having a sleevelike housing part having a substantially cylindrical inner wall which closely surrounds the peripheral wall of said rotor, said cylindrical inner wall projecting axially beyond the one axial end surface of the rotor and defining an enlarged annular space which defines one end of said passage for communication with the outlet openings associated with said recesses, said passage projecting axially outwardly of said turbine housing from said space.

11. An assembly according to claim 8, wherein the surrounding peripheral wall of the rotor is substantially cylindrical, said recesses projecting inwardly of the rotor from said peripheral wall, said recesses terminating in a substantially flat bottom wall so that the individual recesses have a depth which is small relative to the cross-section of the recess as measured both circumferentially and axially relative to the rotor, the peripheral side wall of the recess causing the jet of fluid which impacts against the front concave wall portion to be exhausted substantially axially of the rotor through the outlet opening into the discharge passage, said discharge passage including a nonrestricted annular passage which is positioned axially adjacent said one axial end surface of the rotor and is in continuous communication with the outlet openings of said recesses for permitting unrestricted discharge of the fluid from the recesses through the respective outlet openings.

* * * * *